US012322498B2

(12) United States Patent
Yamada

(10) Patent No.: US 12,322,498 B2
(45) Date of Patent: Jun. 3, 2025

(54) IMAGE PROCESSING APPARATUS, IMAGE DISPLAY SYSTEM, IMAGE PROCESSING METHOD, AND PROGRAM FOR DISPLAYING INFORMATION ASSOCIATED WITH REGION OF INTEREST OF MEDICAL IMAGE

(71) Applicant: FUJIFILM Corporation, Tokyo (JP)

(72) Inventor: Kenta Yamada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 443 days.

(21) Appl. No.: 17/900,833

(22) Filed: Aug. 31, 2022

(65) Prior Publication Data
US 2022/0415484 A1 Dec. 29, 2022

Related U.S. Application Data

(63) Continuation of application No. PCT/JP2021/007301, filed on Feb. 26, 2021.

(30) Foreign Application Priority Data

Mar. 4, 2020 (JP) .................................. 2020-036936

(51) Int. Cl.
G16H 30/40 (2018.01)
G06T 7/00 (2017.01)
G06T 7/11 (2017.01)

(52) U.S. Cl.
CPC ........... *G16H 30/40* (2018.01); *G06T 7/0012* (2013.01); *G06T 7/11* (2017.01)

(58) Field of Classification Search
CPC .......... G16H 30/40; G06T 7/11; G06T 7/0012
(Continued)

(56) References Cited

U.S. PATENT DOCUMENTS 11,282,198 B2 * 3/2022 Lyman .................. G16H 40/67
11,563,921 B2 * 1/2023 Kamon ................ A61B 1/0646
(Continued)

FOREIGN PATENT DOCUMENTS

JP 2004173910 6/2004
JP 2008152333 7/2008
(Continued)

OTHER PUBLICATIONS

Office Action of Japan Counterpart Application, with English translation thereof, issued on Aug. 8, 2023, pp. 1-8.
(Continued)

*Primary Examiner* — Allen H Nguyen
(74) *Attorney, Agent, or Firm* — JCIPRNET

(57) ABSTRACT

An image processing apparatus, an image display system, an image processing method, and a program by which it is possible to grasp, on a screen for observing a given low-dimensional image having a lower level of dimensions than a medical image, information of the low-dimensional image in which a region of interest is present and information of the region of interest. A medical image including two or more low-dimensional images (102) is acquired, region-of-interest information representing information of a region of interest (108) automatically detected from the medical image is acquired for each of the low-dimensional images, axis information (104) representing a space axis or a time axis is generated, additional information (106) associated with the axis information is generated, the additional information including presence information indicating that the region of interest is present and content information indicating content of the region of interest, and the low-dimensional images, the axis information, and the additional information are displayed on a display.

14 Claims, 13 Drawing Sheets

(58) Field of Classification Search
USPC .......................................................... 382/128
See application file for complete search history.

(56) References Cited

U.S. PATENT DOCUMENTS

| | | | |
|---|---|---|---|
| 11,954,598 B2* | 4/2024 | Lisowska | ................ G06F 16/51 |
| 2010/0141654 A1 | 6/2010 | Neemuchwala et al. | |
| 2011/0109650 A1 | 5/2011 | Kreeger et al. | |
| 2013/0084246 A1* | 4/2013 | Moats | ................... G06T 7/0012 |
| | | | 382/128 |
| 2013/0249903 A1 | 9/2013 | Isokawa et al. | |
| 2020/0074712 A1* | 3/2020 | Wu | ....................... G06V 10/454 |
| 2022/0005584 A1* | 1/2022 | Takahashi | ............. G06V 30/194 |
| 2023/0071400 A1* | 3/2023 | Abdolell | ................ G16H 30/20 |

FOREIGN PATENT DOCUMENTS

| | | |
|---|---|---|
| JP | 2009230468 | 10/2009 |
| JP | 2015171456 | 10/2015 |
| WO | 2012049741 | 4/2012 |

OTHER PUBLICATIONS

"Office Action of Japan Counterpart Application", issued on Aug. 6, 2024, with English translation thereof, p. 1-p. 7.

"International Search Report (Form PCT/ISA/210) of PCT/JP2021/007301," mailed on Apr. 13, 2021, with English translation thereof, pp. 1-5.

"Written Opinion of the International Searching Authority (Form PCT/ISA/237)" of PCT/JP2021/007301, mailed on Apr. 13, 2021, with English translation thereof, pp. 1-8.

* cited by examiner

IMAGE PROCESSING APPARATUS, IMAGE DISPLAY SYSTEM, IMAGE PROCESSING METHOD, AND PROGRAM FOR DISPLAYING INFORMATION ASSOCIATED WITH REGION OF INTEREST OF MEDICAL IMAGE

CROSS-REFERENCE TO RELATED APPLICATIONS

The present application is a Continuation of PCT International Application No. PCT/JP2021/007301 filed on Feb. 26, 2021 claiming priority under 35 U.S.C § 119(a) to Japanese Patent Application No. 2020-036936 filed on Mar. 4, 2020. Each of the above applications is hereby expressly incorporated by reference, in its entirety, into the present application.

BACKGROUND OF THE INVENTION

1. Field of the Invention

The present invention relates to an image processing apparatus, an image display system, an image processing method, and a program.

2. Description of the Related Art

In recent medical image diagnosis, many image diagnosis support functions for detecting diseases such as cerebral aneurysm, pulmonary nodule, and breast cancer have been studied. For example, a cerebral aneurysm, a pulmonary nodule, and the like can be detected using a three dimensional medical image generated by computed tomography (CT), magnetic resonance imaging (MRI), and the like.

In medical image diagnosis using a three dimensional medical image, there is a tendency that the number of images to be checked increases and a work load in interpretation or the like increases. Therefore, in medical image diagnosis using a three dimensional medical image, it is expected to reduce a work load such as interpretation due to an image diagnosis support function. In some cases, the image diagnosis support function is expressed using CAD, which is an abbreviation of the English notation for computer-aided diagnosis.

JP2015-171456A describes a medical image display apparatus that detects an anatomic position from a medical image composed of a plurality of slice images, generates an interpretation guide based on the anatomic position, and displays the interpretation guide.

JP2015-171456A describes a display mode of a medical image in which a bar corresponding to the total number of slices is displayed beside a given slice image, a mark indicating a region to be interpreted is displayed beside the bar, and a slider indicating the current position of the medical image is displayed.

WO2012/049741A describes a medical image display apparatus that displays diagnostic information of a region of interest on a portion of a screen on which a medical image is displayed. WO2012/049741A describes diagnostic information that is arranged in order of importance.

SUMMARY OF THE INVENTION

However, it is difficult to visually recognize at a glance where a lesion detected using CAD is located in a displayed image. Furthermore, there is a possibility that a work load increases when it is all checked whether or not a detected object is a lesion and whether or not follow-up, treatment, or the like should be performed in a case where the detected object is a lesion.

In the apparatus described in JP2015-171456A, when a local structure corresponding to an anatomic position is interpreted, it is possible to grasp the order of interpretation and the relative positional relationship between displayed slice images and the position of an interpretation target, but it is difficult to grasp the position of a region of interest in a medical image and information on the region of interest.

In the apparatus described in WO2012/049741A, the diagnostic information is sorted in order of priority, and the positions of the respective slice images in the three dimensional image are interchanged. In this case, it is difficult to grasp which slice image in the three dimensional image corresponds to the diagnostic information from a display screen of the slice images.

The present invention has been made in view of such circumstances, and an object thereof is to provide an image processing apparatus, an image display system, an image processing method, and a program by which it is possible to grasp information of a low-dimensional plane image in which a region of interest is present and information of the region of interest on a screen for observing a given low-dimensional image having a lower level of dimensions than a medical image.

In order to achieve the above object, the following aspects of the invention are provided.

An image processing apparatus according to the present disclosure is an image processing apparatus including one or more processors, in which the processor acquires a medical image obtained by imaging a subject, the medical image including two or more low-dimensional images having a lower level of dimensions than the medical image, acquires region-of-interest information, for each of the low-dimensional images, representing information of a region of interest automatically detected from the medical image, generates axis information representing a space axis or a time axis in the low-dimensional images, generates additional information associated with the axis information, the additional information including presence information indicating that the region of interest is present and content information indicating content of the region of interest, and outputs a display image signal for displaying the low-dimensional images, the axis information, and the additional information on a display.

According to the image processing apparatus according to the present disclosure, in the medical image including the plurality of low-dimensional images, it is possible to grasp the position of a low-dimensional images including the region of interest and to grasp the content of the region of interest for each of the low-dimensional images.

An example of the low-dimensional images is a two dimensional image generated from a three dimensional image. An example of the two dimensional image is a two dimensional cross-sectional image. Another example of the low-dimensional images is a three dimensional image generated from four dimensional images in which three dimensional images are arranged along the time axis.

Acquiring the medical image including the two or more low-dimensional images may include acquiring a three dimensional image including two or more two dimensional images and generating a plurality of two dimensional images from the acquired three dimensional image. Acquiring the region-of-interest information may include the concept of generating the region-of-interest information.

In an image processing apparatus according to another aspect, the processor generates a slider bar representing the space axis or a slider bar representing the time axis, as the axis information.

According to this aspect, the space axis or the time axis can be displayed on a display screen of the low-dimensional images using the slider bar.

In an image processing apparatus according to another aspect, the processor generates the presence information representing a position on the space axis of the medical image where the region of interest is present or a position on the time axis of the medical image where the region of interest is present.

According to this aspect, it is possible to grasp the low-dimensional images in which the region of interest is present from the presence information given to the space axis or the time axis.

In an image processing apparatus according to another aspect, the processor generates the additional information such that a symbol is applied to the presence information and a form of the symbol is used to represent a degree in the content information.

According to this aspect, it is possible to grasp the low-dimensional images in which the region of interest is present and the degree of the region of interest on the basis of the symbol.

In an image processing apparatus according to another aspect, the processor generates the additional information including the content information whose degree is represented using at least one of a size of the symbol, a number of symbols, or a color of the symbol.

According to this aspect, it is possible to grasp the degree of the region of interest on the basis of at least one of the size of the symbol, the number of symbols, or the color of the symbol.

In an image processing apparatus according to another aspect, the processor generates the presence information in which a plurality of symbols are represented as one generic symbol.

According to this aspect, it is possible to grasp the presence of the plurality of symbols even if the plurality of symbols overlap each other.

In an image processing apparatus according to another aspect, if an operation of selecting the generic symbol is performed, the processor generates the presence information in which the plurality of symbols corresponding to the generic symbol are displayed in an enlarged manner.

According to this aspect, it is possible to individually grasp the plurality of symbols represented using the generic symbol.

In an image processing apparatus according to another aspect, if the region-of-interest information at a time of detection of a lesion as the region of interest is acquired, the processor generates the additional information including at least one of a severity of a disease corresponding to the lesion, a priority of diagnosis of the lesion, or a certainty factor of the automatic detection, as the content information.

According to this aspect, if the region of interest is a lesion, it is possible to grasp at least one of the severity of the disease corresponding to the lesion, the priority of diagnosis of the lesion, or the certainty factor of the automatic detection.

An image display system according to the present disclosure is an image display system including an image processing apparatus including one or more processors; and a display that receives a display image signal transmitted from the image processing apparatus and displays an image represented by the display image signal, in which the processor acquires a medical image obtained by imaging a subject, the medical image including two or more low-dimensional images having a lower level of dimensions than the medical image, acquires region-of-interest information, for each of the low-dimensional images, representing information of a region of interest automatically detected from the medical image, generates axis information representing a space axis or a time axis in the low-dimensional images, generates additional information associated with the axis information, the additional information including presence information indicating that the region of interest is present and content information indicating content of the region of interest, and outputs a display image signal for displaying the low-dimensional images, the axis information, and the additional information on the display.

An image processing method according to the present disclosure is an image processing method including: acquiring a medical image obtained by imaging a subject, the medical image including two or more low-dimensional images having a lower level of dimensions than the medical image; acquiring region-of-interest information, for each of the low-dimensional images, representing information of a region of interest automatically detected from the medical image; generating axis information representing a space axis or a time axis in the low-dimensional images; generating additional information associated with the axis information, the additional information including presence information indicating that the region of interest is present and content information indicating content of the region of interest; and outputting a display image signal for displaying the low-dimensional images, the axis information, and the additional information on a display.

A program according to the present disclosure is a program for causing a computer to implement: a medical image acquisition function of acquiring a medical image obtained by imaging a subject, the medical image including two or more low-dimensional images having a lower level of dimensions than the medical image; a region-of-interest information acquisition function of acquiring region-of-interest information, for each of the low-dimensional images, representing information of a region of interest automatically detected from the medical image; an axis information generation function of generating axis information representing a space axis or a time axis in the low-dimensional images; an additional information generation function of generating additional information associated with the axis information, the additional information including presence information indicating that the region of interest is present and content information indicating content of the region of interest; and a display image signal output function of outputting a display image signal for displaying the low-dimensional images, the axis information, and the additional information on a display.

According to the present invention, it is possible to grasp, in a medical image including a plurality of low-dimensional images, positions of the low-dimensional images including a region of interest, and to grasp the content of the region of interest for each of the low-dimensional images.

DESCRIPTION OF THE PREFERRED EMBODIMENTS

Figure 1:
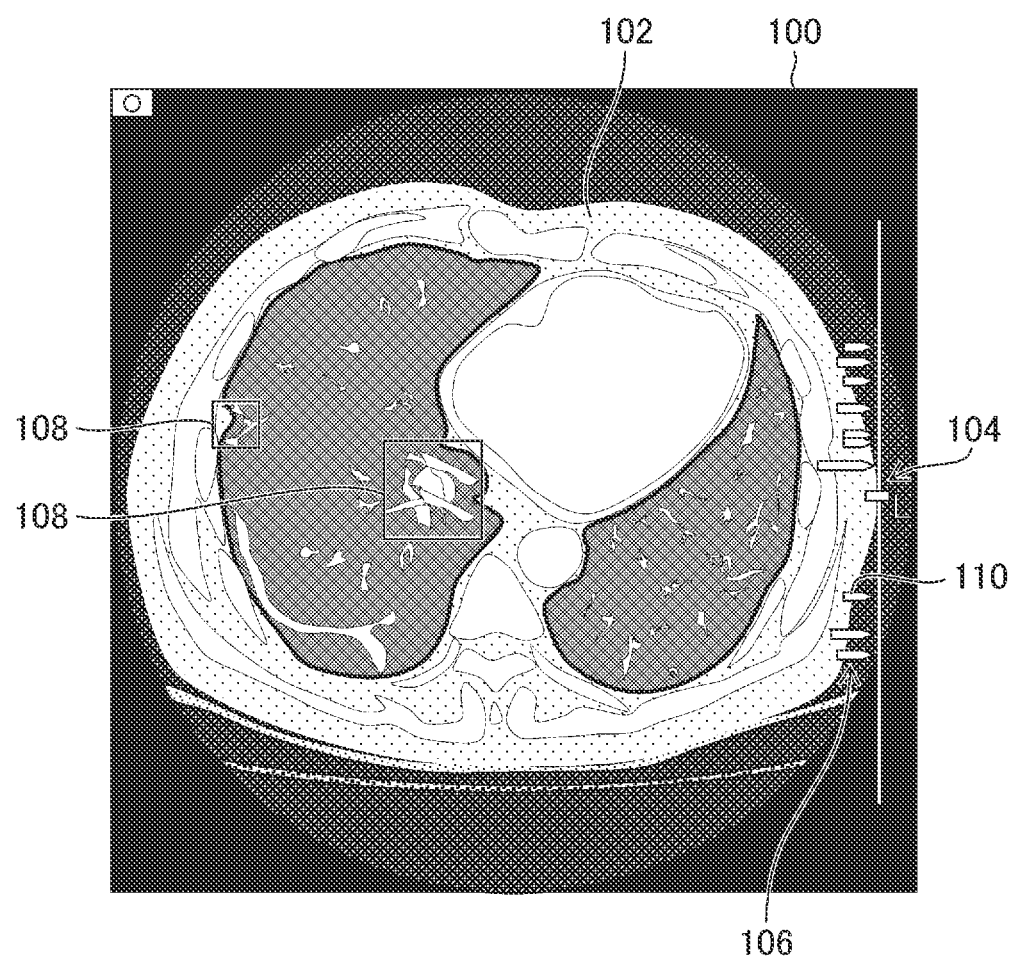
FIG. 1 is a schematic diagram of a medical image display screen.

Hereinafter, a preferred embodiment of the present invention will be described in detail with reference to the accompanying drawings. In the present specification, the same components are denoted by the same reference numerals, and overlapping description will be appropriately omitted.

Configuration Example of Medical Image Display System

[Outline of Medical Image Display Screen]

FIG. 1 is a schematic diagram of a medical image display screen. A slice image 102 of lungs is displayed on a medical image display screen 100 illustrated in FIG. 1. The medical image display screen 100 displays a slider bar 104 indicating a Z direction in a case where a two dimensional cross section corresponding to the slice image 102 is an XY plane in a three dimensional orthogonal coordinate system.

The slider bar 104 includes a bar indicating a range in which all slice images 102 are included and a slider indicating the position, in the entire range, of the slice image 102 displayed on the medical image display screen 100. The slider bar 104 described in the embodiment is an example of axis information.

An annotation 106 is also displayed on the medical image display screen 100. The annotation 106 represents the position, in the three dimensional image, of the slice image 102 where a region of interest 108 automatically detected using CAD is present. FIG. 1 illustrates the slice image 102 including two regions of interest 108.

The annotation 106 includes a plurality of arrow symbols 110. The respective positions of the plurality of arrow symbols 110 represent positions, in the slider bar 104, of slice images 102 where regions of interest 108 are present. When a user such as a doctor clicks any given one of the plurality of arrow symbols 110, a slice image 102 corresponding to the arrow symbol 110 clicked by the user is displayed on the medical image display screen 100.

Figure 2:
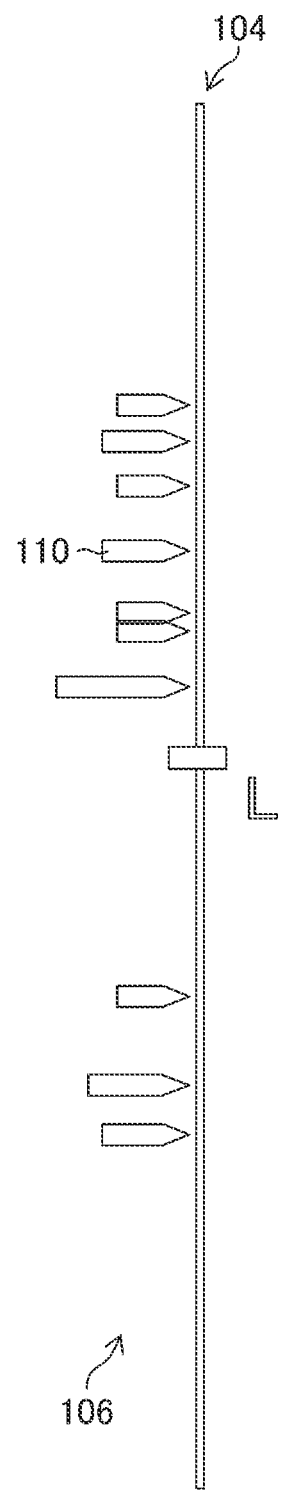
FIG. 2 is an enlarged view of a slider bar and an annotation.

FIG. 2 is an enlarged view of the slider bar and the annotation. In the annotation 106 illustrated in FIG. 2, the design of the arrow symbols 110 is changed depending on the sizes of the regions of interest 108 illustrated in FIG. 1. In the example illustrated in FIG. 2, as the sizes of the regions of interest 108 are relatively large, the lengths of the plurality of arrow symbols 110 are relatively long.

That is, the arrow symbols 110 constituting the annotation 106 have forms corresponding to the degrees of the regions of interest 108. If a region of interest 108 is a lesion, a severity of a disease corresponding to the lesion, a priority of diagnosis, a detection certainty factor of CAD, or the like can be applied as the degree of the region of interest 108.

For example, if the severity of the disease corresponding to the lesion is relatively high, the lengths of the plurality of arrow symbols 110 may be relatively long. If the severity of the disease corresponding to the lesion is relatively high, the areas of the plurality of arrow symbols 110 may be relatively large.

The arrow symbols 110 constituting the annotation 106 may have sizes corresponding to the priority of diagnosis, the detection certainty factor of CAD, or the like. Note that the sizes of the arrow symbols 110 are a comprehensive concept of the lengths of the arrow symbols 110 and the areas of the arrow symbols 110.

Change in the design of the arrow symbols 110 may apply color and gradation. For example, if the sizes of the regions of interest 108 have three levels of large, medium, and small, the colors of the arrow symbols 110 may be red, green, and blue. The change in the design of the plurality of arrow symbols 110 may be any change that can be visually distinguished by the user.

Figure 3:
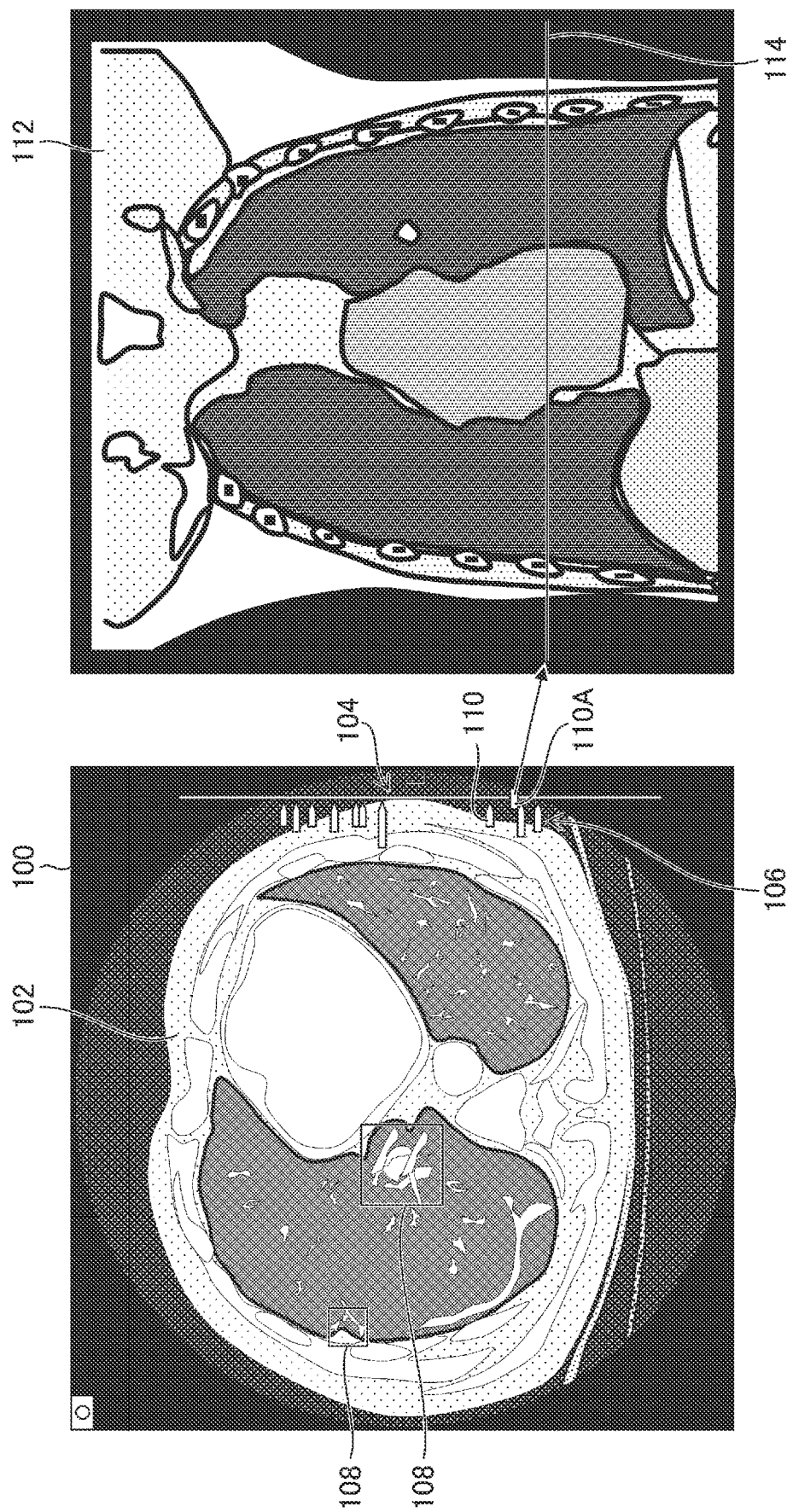
FIG. 3 is an explanatory diagram illustrating a correspondence relationship between the annotation and a cross-sectional position.

FIG. 3 is an explanatory diagram illustrating a correspondence relationship between the annotation and a cross-sectional position. FIG. 3 illustrates a coronal image 112 corresponding to the slice image 102 that is an axial image. FIG. 3 illustrates a cross-sectional position 114 corresponding to an arrow symbol 110A in the coronal image 112. That is, if the user clicks the arrow symbol 110A illustrated in the left drawing of FIG. 3, the slice image 102 at the cross-sectional position 114 illustrated in the right drawing of FIG. 3 is displayed on the medical image display screen 100.

Although a three dimensional image composed of a plurality of slice images 102 along a space axis is exemplified as a medical image in the present embodiment, the medical image may be a three dimensional image composed of a plurality of slice images 102 along a time axis.

In addition, the medical image may be a four dimensional image composed of a plurality of three dimensional images along the time axis. Note that the slice image 102 illustrated in the embodiment is an example of a low-dimensional image having a lower level of dimensions than a medical image.

Although the slider bar 104 corresponding to the Z direction in the slice image on the XY plane is exemplified in this embodiment, the slider bar is not limited to the display of the space axis. For example, a slider bar representing a time axis may be applied.

Although the annotation 106 to which the arrow symbols 110 are applied is exemplified in the present embodiment, a symbol such as a balloon may also be used as the annotation 106.

Note that the annotation 106 described in the embodiment corresponds to an example of additional information associated with axis information. The arrow symbols 110 are each an example of presence information indicating that a region of interest is present. The number of arrow symbols 110 described in the embodiment is an example of content information.

[Overall Configuration of Medical Image Display System]

Figure 4:
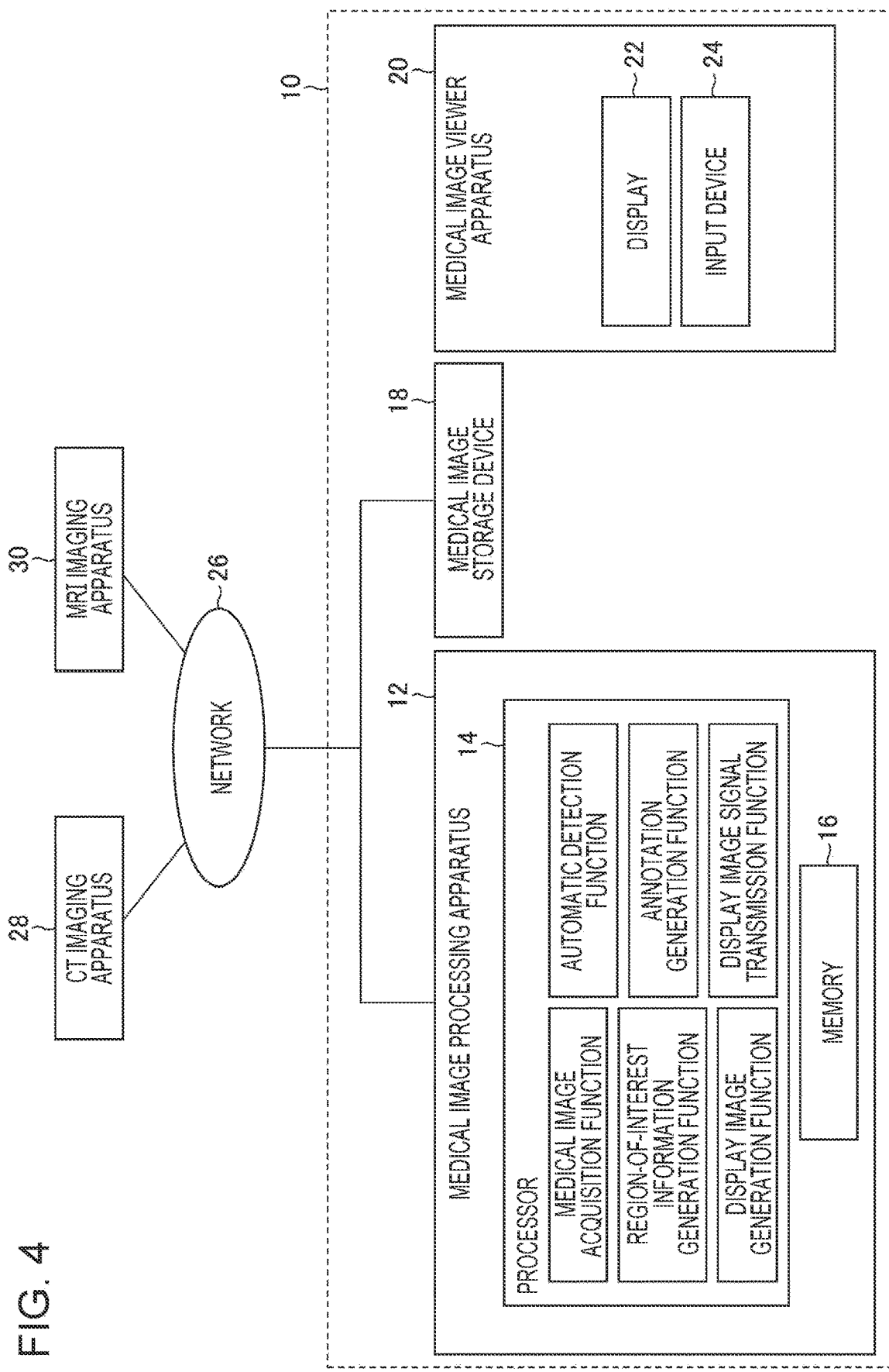
FIG. 4 is a functional block diagram of a medical image display system according to an embodiment.

FIG. 4 is a functional block diagram of a medical image display system according to the embodiment. A medical image display system 10 includes a medical image processing apparatus 12, a medical image storage device 18, and a medical image viewer apparatus 20.

The medical image processing apparatus 12 is a terminal apparatus used by a user in a hospital, an examination laboratory, or the like. A computer is applicable as the medical image processing apparatus 12. The medical image processing apparatus 12 includes a processor 14 and a memory 16.

The memory 16 includes a program memory in which programs including instructions to be executed by the processor 14 are stored. The memory 16 may include a data memory in which various types of data are stored.

The medical image processing apparatus 12 executes programs read out by the processor 14 from the memory 16, and implements various functions including a medical image acquisition function, an automatic detection function, a region-of-interest information generation function, an annotation generation function, a display image generation function, and a display image signal transmission function.

The term "image" may be used to refer to an image signal and image data representing an image. The term "generation" can be read as "creation", "production", and the like. Furthermore, the display image signal transmission function may be read as a display image output function. Note that the processor 14 described in the embodiment is an example of one or more processors.

The medical image storage device 18 stores medical images to which accessory information defined by the DICOM standard is added. The medical image may be raw data acquired using a modality such as a CT imaging apparatus 28 or an MRI imaging apparatus 30 for imaging a subject, or may be volume data generated from the raw data. A large-capacity storage device is applicable as the medical image storage device 18. Note that DICOM is an abbreviation of Digital Imaging and Communication in Medicine.

The medical image viewer apparatus 20 is used when a user observes a medical image. The slice image 102 illustrated in FIG. 1 is applicable as the medical image at the time of observation. The medical image viewer apparatus 20 includes a display 22 and an input device 24.

The display 22 displays an image represented by a display image signal acquired from the medical image processing apparatus 12. The display 22 can display a medical image stored in the medical image storage device 18 on the basis of a command from the medical image processing apparatus 12.

The input device 24 transmits an input signal corresponding to an operation of the user to the medical image processing apparatus 12. An operating member such as a keyboard, a mouse, or a joystick is applicable as the input device 24. The display 22 and the input device 24 may be integrally configured by applying the display 22 of a touch panel type.

The medical image display system 10 is communicably connected to a modality such as the CT imaging apparatus 28 via a network 26. A local area network (LAN) is applicable as the network 26. An in-house LAN in a hospital or the like is applicable as the network 26. The network 26 may include an external network of a hospital or the like.

The modality may include a PET apparatus, an ultrasound diagnostic apparatus, a CR apparatus, and the like. Note that PET is an abbreviation of Positron Emission Tomography. CR is an abbreviation for Computed Radiography.

[Procedure of Medical Image Processing Method]

Figure 5:
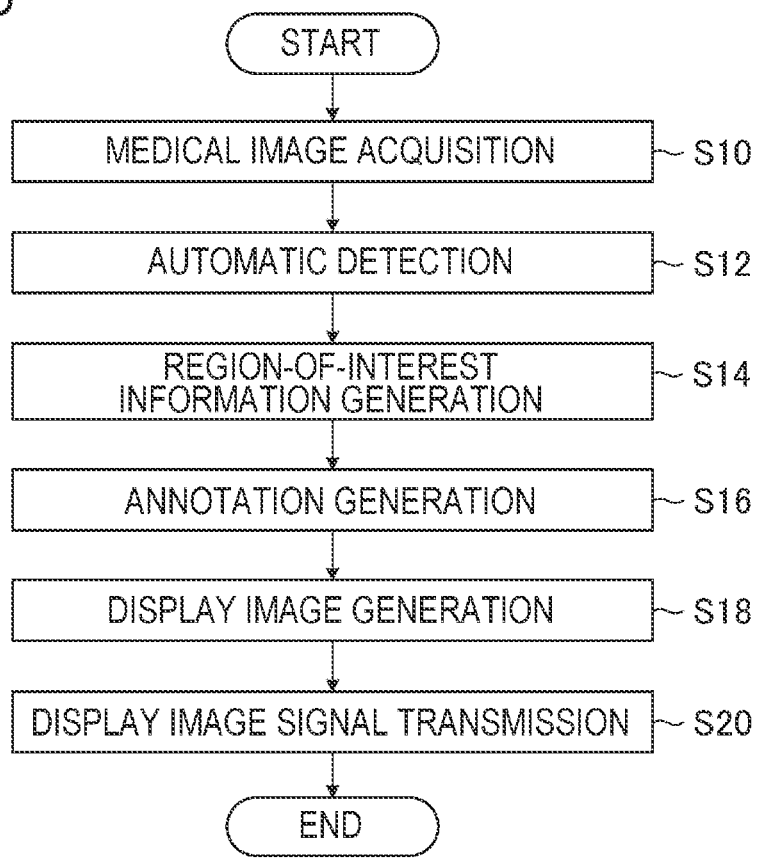
FIG. 5 is a flowchart illustrating a procedure of a medical image processing method according to the embodiment.

FIG. 5 is a flowchart illustrating a procedure of a medical image processing method according to the embodiment. In medical image acquisition step S10, the processor 14 acquires a medical image that is a processing target from the medical image storage device 18 or the like.

The medical image may be acquired by acquiring data in a format that can be processed by the processor 14, or by acquiring data in any given format and converting the data into data in a format that can be processed by the processor 14. For example, if the slice image 102 illustrated in FIG. 1 is a processing target, the processor 14 may acquire the slice image 102, or may acquire a three dimensional image and generate the slice image 102 from the three dimensional image. After medical image acquisition step S10, the process proceeds to automatic detection step S12.

In automatic detection step S12, the processor 14 performs automatic detection of a region of interest 108 for each acquired slice image 102. A known method is applicable as the automatic detection of the region of interest 108. For example, the processor 14 may perform automatic detection of the region of interest 108 for each slice image 102 by applying segmentation to extract a region having regularity from the image. After automatic detection step S12, the process proceeds to region-of-interest information generation step S14.

In medical image acquisition step S10, a medical image in which the region of interest 108 has been automatically detected may be acquired. In such a case, instead of automatic detection step S12, the processor 14 performs a process of reading out the region of interest 108 for each slice image 102 from the acquired medical image as automatic detection of the region of interest 108.

In region-of-interest information generation step S14, the processor 14 generates region-of-interest information for each slice image 102. The size of the region of interest 108, the severity of the disease in the lesion, and the priority of the diagnosis are applicable as the region-of-interest information. Note that the generation of the region-of-interest information for each slice image 102 described in the embodiment is an example of acquisition of the region-of-interest information for each low-dimensional image.

Examples of the size of the region of interest 108 include the long diameter and the area of the region of interest 108, the size of a bounding box surrounding the region of interest 108, and the like. The length of the major axis in a case where the region of interest 108 is elliptically approximated is applicable as the long diameter of the region of interest 108. The maximum value of the distance between any given two points on the outer shape of the region of interest 108 passing through the center of gravity of the region of interest 108 is applicable as the long diameter of the region of interest 108.

The severity of the disease can be grasped from a change in the size of the lesion in comparison with the past, a change in the state of the lesion in comparison with the past, or the like. The severity of the disease may be defined on the basis of a severity evaluation value obtained by digitizing the severity of the lesion.

The priority of diagnosis can be defined in terms of whether or not the lesion is a lesion being compared in the past. A priority defined in advance for each lesion is applicable as the priority of diagnosis. A certainty factor of automatic detection is applicable as the region-of-interest information. After region-of-interest information generation step S14, the process proceeds to annotation generation step S16.

In annotation generation step S16, the processor 14 generates an annotation for each slice image 102 and for each region of interest 108. The processor 14 may generate annotations for a plurality of perspectives. For example, the processor 14 may generate an annotation in terms of the size of region of interest 108 and an annotation in terms of the severity of the disease. The processor 14 may generate an annotation representing an overall evaluation for a plurality of viewpoints. After annotation generation step S16, the process proceeds to display image generation step S18.

In display image generation step S18, a display image to be displayed on the medical image display screen 100 illustrated in FIG. 1 is generated. The medical image display screen 100 illustrated in FIG. 1 includes the slice image 102, the slider bar 104, and the annotation 106 as the display image.

That is, the processor 14 generates the slider bar 104 to be superimposed and displayed on a given slice image 102 on the basis of information such as the slice thickness and the slice interval in a plurality of slice images 102. In addition, the processor 14 generates the annotation 106 to be superimposed and displayed on a given slice image 102 on the basis of the region-of-interest information in each of the slice images 102. After display image generation step S18, the process proceeds to display image signal transmission step S20.

In display image signal transmission step S20, the processor 14 transmits a display image signal corresponding to the display image to the medical image viewer apparatus 20. After display image signal transmission step S20, the processor 14 ends the procedure of the image processing method.

The medical image viewer apparatus 20 displays the display image on the display 22 on the basis of the received display image signal. When the medical image viewer apparatus 20 receives a user command signal indicating a user command input by the user using the input device 24, the medical image viewer apparatus 20 switches a display image to be displayed on the display 22 in accordance with the user command signal. For example, if a given arrow symbol 110 illustrated in FIG. 1 is clicked, the slice image 102 corresponding to the clicked arrow symbol 110 is displayed on the medical image display screen 100.

[Advantageous Effects of Image Processing Apparatus, Image Display System, and Image Processing Method According to Embodiment]

The image processing apparatus, the image display system, and the image processing method according to the embodiment can obtain the following advantageous effects.

[1]
On the medical image display screen 100, the slider bar 104 corresponding to the Z-axis direction is superimposed and displayed on the slice image 102 on an XY plane in a three dimensional orthogonal coordinate system. On the medical image display screen 100, the annotation 106 corresponding to the degree of the region of interest 108 included in the slice image 102 is also superimposed and displayed for the slice image 102. Accordingly, the user can recognize whether or not the region of interest is present in the medical image to be observed and the degree of the region of interest.

[2]
The annotation 106 is displayed at the position of the corresponding slice image 102 in the slider bar 104. Accordingly, in the observation of the medical image including two or more slice images 102, the user can recognize the slice image 102 having the region of interest 108.

[3]
A display mode representing the content of the region of interest 108 is applied to the annotation 106. Accordingly, the user can grasp the content of the region of interest 108 on the basis of the display mode of the annotation 106.

[4]
As a display mode of the annotation 106, the size, color, gradation, or the like is applied. Accordingly, the user can grasp the content of the region of interest 108 on the basis of the display mode of the annotation 106.

[Modifications of Annotation]

Next, modifications of the annotation 106 illustrated in FIG. 2 and the like will be described.

[First Issue of Annotation]

Figure 6:
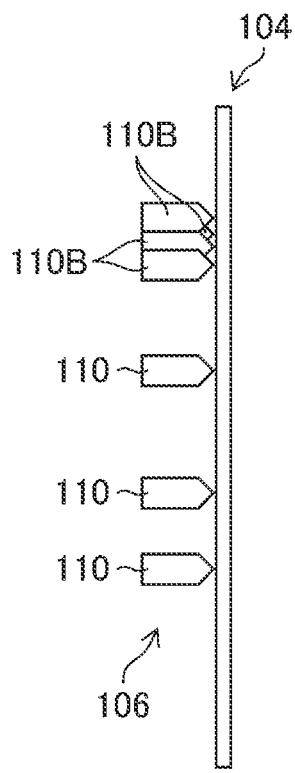
FIG. 6 is an explanatory diagram of a first issue.

FIG. 6 is an explanatory diagram of a first issue. If there are a large number of regions of interest 108 that are detected, or if a region of interest 108 is present in each of the preceding and succeeding slice images 102, for example, a plurality of arrow symbols 110B can be densely arranged. For example, the annotation 106 illustrated in FIG. 6 is arranged such that four arrow symbols 110B overlap each other.

In such a display mode of the annotation 106, there is an issue that it is difficult for a user to grasp each of the dense arrow symbols 110B and to perform an operation when clicking an arrow symbol 110B. An annotation according to a first modification can address such an issue and ensure user's convenience.

[Annotation According to First Modification]

Figure 7:
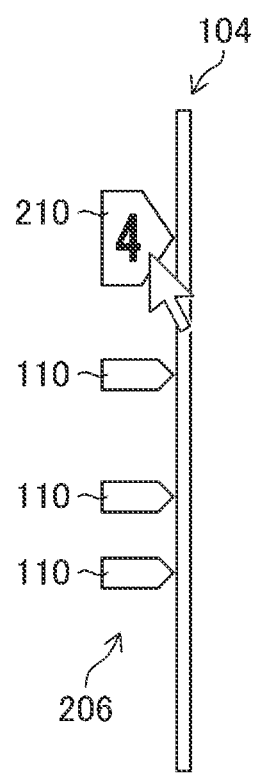
FIG. 7 is a schematic diagram of an annotation according to a first modification.

FIG. 7 is a schematic diagram of the annotation according to the first modification. An annotation 206 illustrated in FIG. 7 includes an integrated arrow symbol 210 in which a plurality of arrow symbols 110B are integrated. The numerical value 4 indicating an integration number of arrow symbols 110 is superimposed and displayed on the integrated arrow symbol 210. Furthermore, the integrated arrow symbol 210 has a size corresponding to the arrangement area of the integrated arrow symbols 110.

Figure 8:
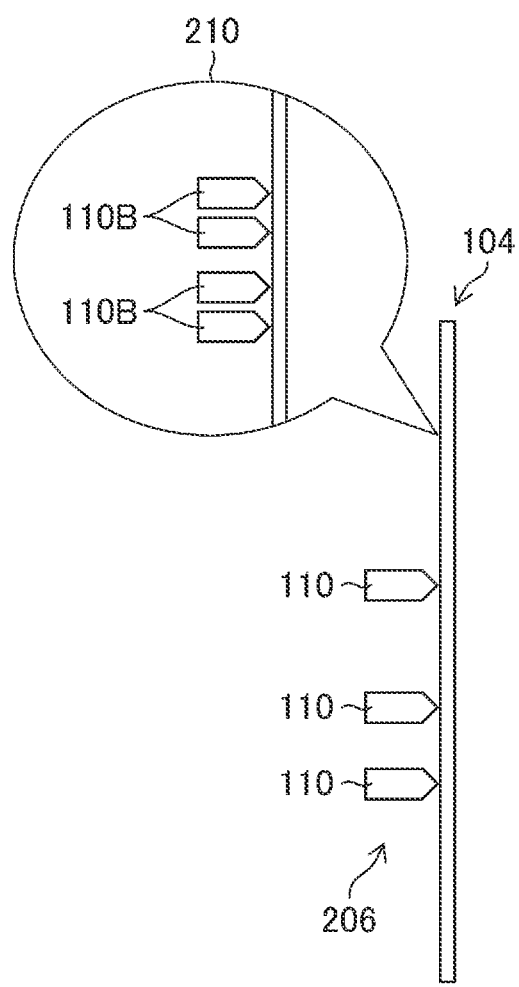
FIG. 8 is an explanatory diagram of the annotation according to the first modification.

FIG. 8 is an explanatory diagram of the annotation according to the first modification. FIG. 8 illustrates a display mode of the annotation 206 after a user has clicked and selected the integrated arrow symbol 210 illustrated in FIG. 7. In the annotation 206 illustrated in FIG. 8, the four arrow symbols 110B included in the integrated arrow symbol 210 are displayed in an enlarged manner.

In the enlarged display of the four arrow symbols 110B illustrated in FIG. 8, the four arrow symbols 110B are arranged so as not to overlap each other. Accordingly, a user can individually grasp the four arrow symbols 110B, and an operation when clicking the four arrow symbols 110B becomes easy. The integrated arrow symbol 210 illustrated in the embodiment is an example of a generic symbol.

[Second Issue of Annotation]

Figure 9:
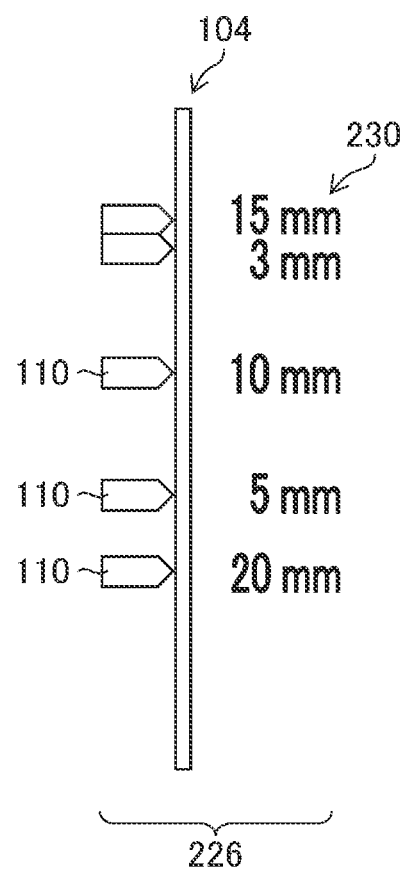
FIG. 9 is an explanatory diagram of a second issue.

FIG. 9 is an explanatory diagram of a second issue. The size of the annotation 106 illustrated in FIG. 2 and the like can be changed depending on the size of the region of interest 108. Furthermore, the annotation 106 may represent the size of the region of interest 108. For example, an annotation 226 illustrated in FIG. 9 includes size information 230 of the region of interest 108 for each arrow symbol 110.

However, although the size information 230 illustrated in FIG. 9 directly represents the size of the region of interest 108 by applying character information, and the size of the region of interest 108 can be grasped at a glance, the medical image display screen 100 becomes complicated. In addition, if the size information 230 is displayed in a small size, the visibility of the size information 230 decreases.

[Annotation According to Second Modification]

Figure 10:
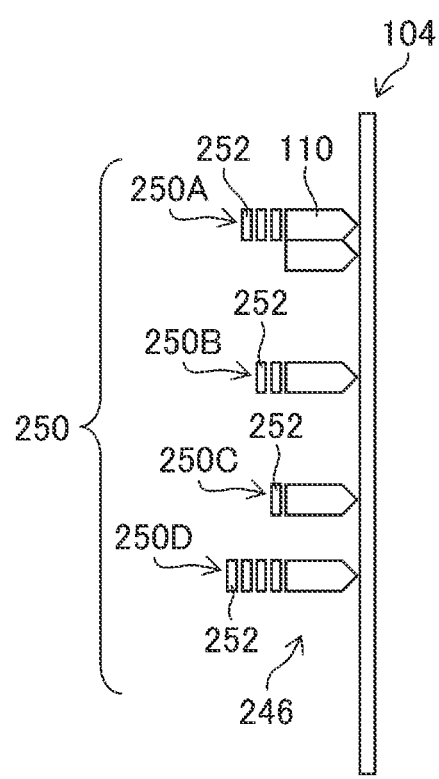
FIG. 10 is a schematic diagram of an annotation according to a second modification.

FIG. 10 is a schematic diagram of an annotation according to a second modification. In an annotation 246 illustrated in FIG. 10, a size display symbol 250 that indirectly indicates the size of the region of interest 108 is added to an arrow symbol 110.

The size display symbol 250 includes one or more square symbols 252. In the size display symbol 250 illustrated in FIG. 10, one square symbol 252 represents 5 millimeters. That is, a size display symbol 250A represents 15 millimeters or more and less than 20 millimeters.

Furthermore, a size display symbol 250B represents 10 millimeters or more and less than 15 millimeters. A size display symbol 250C represents 5 millimeters or more and less than 10 millimeters. A size display symbol 250D represents 20 millimeters or more and less than 25 millimeters. If the size of the region of interest 108 is less than 5 millimeters, the square symbol 252 is not assigned.

Figure 11:
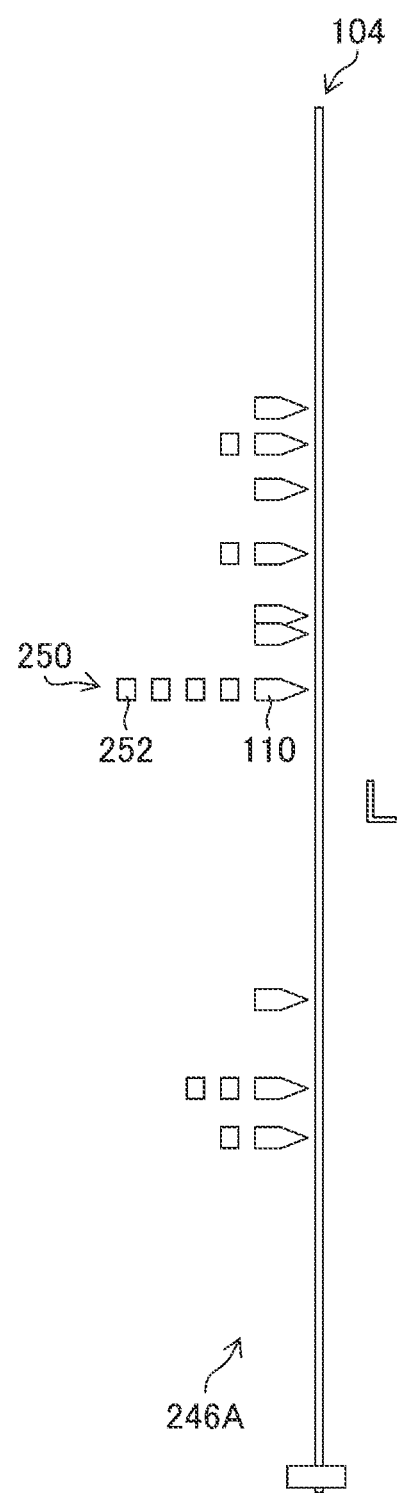
FIG. 11 is a schematic diagram of an annotation illustrating another aspect of the annotation according to the second modification.

FIG. 11 is a schematic diagram of an annotation illustrating another aspect of the annotation according to the second modification. In an annotation 246A illustrated in FIG. 11, as compared with the annotation 246 illustrated in FIG. 10, the interval between the square symbols 252 is widened, and the interval between the square symbols 252 is equal to the width of the square symbols 252.

Figure 12:
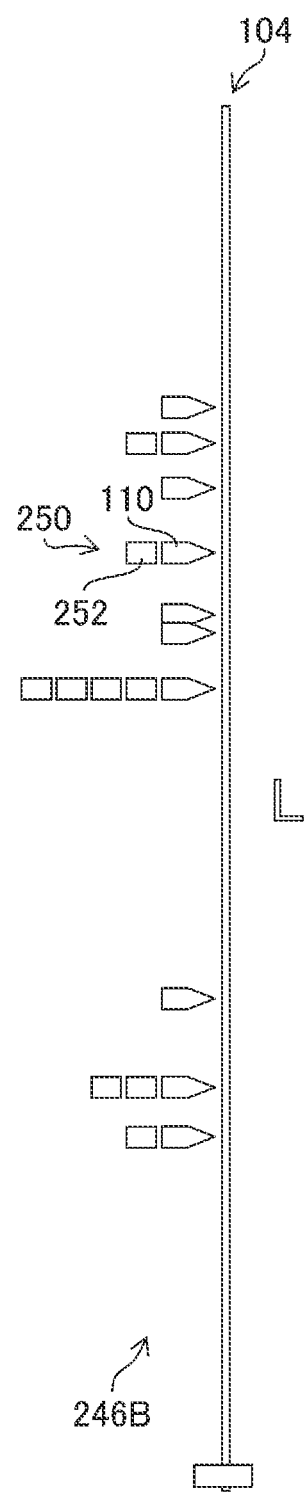
FIG. 12 is a schematic diagram of an annotation illustrating still another aspect of the annotation according to the second modification.

FIG. 12 is a schematic diagram of an annotation illustrating still another aspect of the annotation according to the second modification. In an annotation 246B illustrated in FIG. 12, the width of the square symbols 252 is equal to the width of the arrow symbols 110.

According to the annotation 246 and the like according to the second modification, the size display symbol 250 indicating the size of the region of interest 108 is added to the arrow symbol 110. Thus, a user can grasp the size of the region of interest 108 on the basis of the size display symbol 250. In addition, the medical image display screen 100 is organized, and the visibility of the size display symbol 250 can be improved.

[Other Variations of Annotation]

Figure 13:
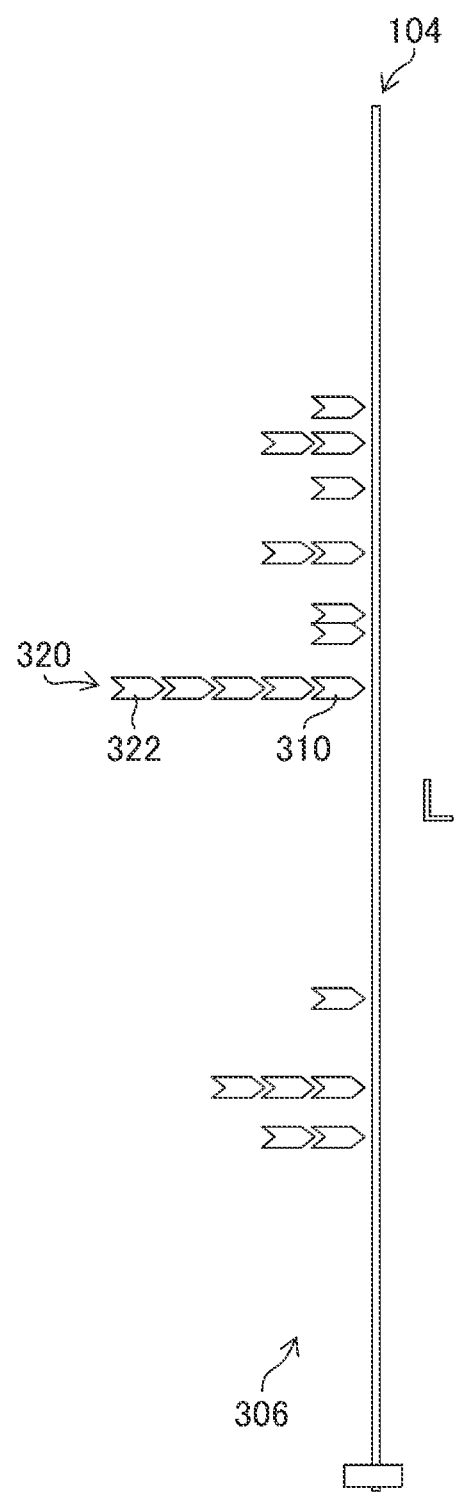
FIG. 13 is a schematic diagram of an annotation according to a third modification.

Next, other variations of the annotation 106 will be exemplified. FIG. 13 is a schematic diagram of an annotation according to a third modification. In an annotation 306 illustrated in FIG. 13, the same form as that of an arrow symbol 310 is applied to a unit symbol 322 constituting a size display symbol 320.

Figure 14:
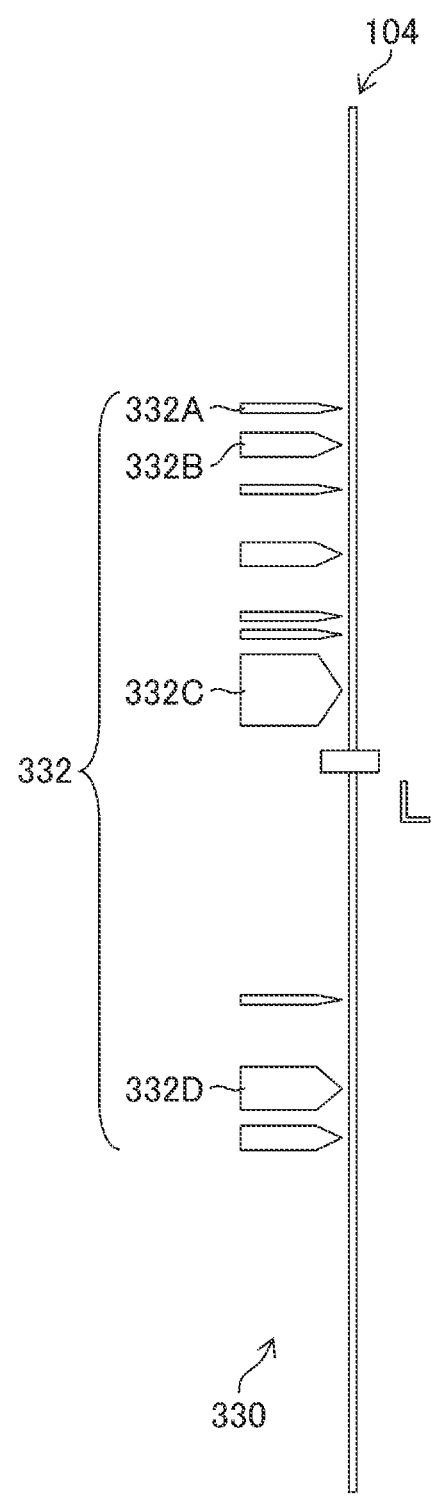
FIG. 14 is a schematic diagram of an annotation according to a fourth modification.

FIG. 14 is a schematic diagram of an annotation according to a fourth modification. An annotation 330 illustrated in FIG. 14 indicates the degree of the region of interest 108 using the area of an arrow symbol 332. For example, an arrow symbol 332A represents 5 millimeters or more and less than 10 millimeters. An arrow symbol 332B represents 10 millimeters or more and less than 15 millimeters. An arrow symbol 332C represents 20 mm or more and less than 25 mm. An arrow symbol 332D represents 15 mm or more and less than 20 mm.

Figure 15:
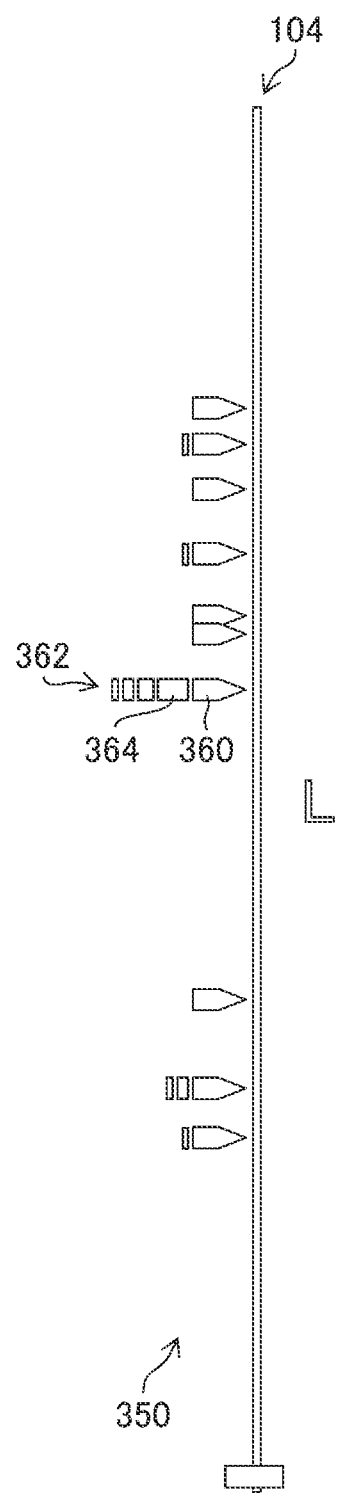
FIG. 15 is an explanatory diagram of an annotation according to a fifth modification.

FIG. 15 is an explanatory diagram of an annotation according to a fifth modification. In an annotation 350 illustrated in FIG. 15, the length of a unit symbol 364 constituting a size display symbol 362 added to an arrow symbol 360 can be changed depending on the number of unit symbols 364.

In the example illustrated in FIG. 15, when the number of unit symbols 364 increases, the length of the unit symbol 364 to be added becomes relatively long. If a plurality of unit symbols 364 are added, the lengths of the unit symbols 364 become relatively shorter in order from the arrow symbol 360 side.

[Hardware Configuration of Processing Units and Control Unit]

A hardware configuration of processing units that execute the processes of the medical image display system 10 and the medical image processing apparatus 12 described in the above embodiment is various processors. The various processors include a central processing unit (CPU), a programmable logic device (PLD), an application specific integrated circuit (ASIC), and the like.

The CPU is a general-purpose processor that executes programs and functions as various processing units. The PLD is a processor whose circuit configuration can be changed after manufacture. An example of the PLD is a field programmable gate array (FPGA). The ASIC is a dedicated electric circuit having a circuit configuration specifically designed to execute a specific process.

One processing unit may be configured by one of these various processors, or may be configured by two or more processors of the same type or different types. For example, one processing unit may be configured using a plurality of FPGAs or the like. One processing unit may be configured by combining one or more FPGAs and one or more CPUs.

In addition, a plurality of processing units may be configured using one processor. As an example of configuring a plurality of processing units using one processor, there is a form in which one processor is configured by combining one or more CPUs and software, and the one processor functions as a plurality of processing units. Such a form is represented by a computer such as a client terminal apparatus or a server apparatus.

As another configuration example, there is a form using a processor that implements the functions of the entire system including a plurality of processing units by using one IC chip. Such a form is represented by a system on chip or the like. Note that IC is an abbreviation of Integrated Circuit. A system on chip may also be referred to as an SoC using an abbreviation of system on chip.

In this manner, various processing units are constituted by one or more of the above various processors in terms of hardware configuration. More specifically, the hardware configuration of various processors is electric circuitry constituted by combining circuit elements such as semiconductor elements.

[Example of Application to Program]

It is possible to configure a program that causes a computer to implement various functions of the medical image display system 10 and the medical image processing apparatus 12 and each step of the image processing method described in the present specification. For example, it is possible to configure a program that causes a computer to implement processing corresponding to the medical image acquisition function, the automatic detection function, the region-of-interest information generation function, the annotation generation function, the display image generation function, and the display image signal transmission function illustrated in FIG. 4.

The display image generation function includes a slider bar generation function of generating the slider bar 104 illustrated in FIG. 1 and the like. The slider bar generation function described in the embodiment is an example of an axis information generation function. The region-of-interest information generation function described in the embodiment is an example of a region-of-interest information acquisition function. The annotation generation function described in the embodiment is an example of an additional information generation function. The display image signal transmission function described in the embodiment corresponds to an example of a display image signal output function.

In the embodiment of the present invention described above, the constituent elements can be changed, added, or deleted as appropriate without departing from the gist of the present invention. The present invention is not limited to the embodiment described above, and various modifications can be made by a person having ordinary knowledge in the art within the technical thought of the present invention. In addition, the embodiment, the modifications, and the application example may be combined and implemented as appropriate.

REFERENCE SIGNS LIST 10 medical image display system
12 medical image processing apparatus
14 processor
16 memory
18 medical image storage device
20 medical image viewer apparatus
22 display
24 input device
26 network
28 CT imaging apparatus
30 MRI imaging apparatus
100 medical image display screen
102 slice image
104 slider bar
106 annotation
108 region of interest
110 arrow symbol
110A arrow symbol
110B arrow symbol
112 coronal image
114 cross-sectional position
206 annotation
210 integrated arrow symbol
226 annotation
230 size information
246 annotation
246A annotation
246B annotation
250 size display symbol
250A size display symbol
250B size display symbol
250C size display symbol
250D size display symbol
252 square symbol
306 annotation
310 arrow symbol
320 size display symbol
322 unit symbol
330 annotation
332 arrow symbol
332A arrow symbol
332B arrow symbol
332C arrow symbol
332D arrow symbol
350 annotation
360 arrow symbol
362 size display symbol
364 unit symbol
S10 to S20 image processing method step

What is claimed is:

1. An image processing apparatus comprising one or more processors, wherein the processor is configured to:
    display a low-dimensional image of a plurality of low-dimensional images obtained from a medical image of a subject, wherein the low-dimensional image is an image of having a lower number of dimensions relative to the medical image,
    display, on the low-dimensional image, a region of interest automatically detected from the medical image,
    display, on or next to the low-dimensional image, an axis along a side of the low dimensional image, and
    display, on or next to the low-dimensional image, an object which corresponds to a location of the axis and expresses information corresponding to the region of interest, wherein the object is a consolidation of multiple objects of a same function as the object, as each of the multiple objects would have represented a different detected region of interest.

2. The image processing apparatus according to claim 1, wherein the axis is a slider bar representing the space axis or a slider bar representing the time axis, as the axis information.

3. The image processing apparatus according to claim 2, wherein the object includes presence information representing a position on the space axis of the medical image where the region of interest is present or a position on the time axis of the medical image where the region of interest is present.

4. The image processing apparatus according to claim 3, wherein the object is a symbol which is applied to the presence information and a form of the symbol is used to represent a degree of content information indicating the region of interest.

5. The image processing apparatus according to claim 4, wherein the degree is represented using at least one of a size of the symbol, a number of symbols, or a color of the symbol.

6. The image processing apparatus according to claim 4, wherein the degree is a size of the region of interest in the low-dimensional images.

7. The image processing apparatus according to claim 4, wherein, if the region-of-interest information at a time of detection of a lesion as the region of interest is acquired, the processor is configured to generate additional information including at least one of a severity of a disease corresponding to the lesion, a priority of diagnosis of the lesion, or a certainty factor of the automatic detection, as the content information.

8. The image processing apparatus according to claim 1, wherein the processor is configured to display a number representing a quantity of the multiple objects consolidated into the object.

9. The image processing apparatus according to claim 8, wherein a length of the object varies in proportion to the quantity of the multiple objects consolidated into the object.

10. The image processing apparatus according to claim 9, wherein, if an operation of selecting the object is performed, the processor generates the presence information in which the multiple objects corresponding to the object are displayed in an enlarged manner.

11. The image processing apparatus according to claim 10, wherein the axis represents the space axis in the low-dimensional images.

12. An image display system comprising:
an image processing apparatus comprising one or more processors; and
a display that receives a display image signal transmitted from the image processing apparatus and displays an image represented by the display image signal,
wherein the processor is configured to:
display a low-dimensional image of a plurality of low-dimensional images obtained from a medical image of a subject, wherein the low-dimensional image is an image of having a lower number of dimensions relative to the medical image,
display, on the low-dimensional image, a region of interest automatically detected from the medical image,
display, on or next to the low-dimensional image, an axis along a side of the low dimensional image, and
display, on or next to the low-dimensional image, an object which corresponds to a location of the axis and expresses information corresponding to the region of interest, wherein the object is a consolidation of multiple objects of a same function as the object, as each of the multiple objects would have represented a different detected region of interest.

13. An image processing method comprising:
displaying a low-dimensional image of a plurality of low-dimensional images obtained from a medical image of a subject, wherein the low-dimensional image is an image of having a lower number of dimensions relative to the medical image;
displaying, on the low-dimensional image, a region of interest automatically detected from the medical image;
displaying, on or next to the low-dimensional image, an axis along a side of the low dimensional image; and
displaying, on or next to the low-dimensional image, an object which corresponds to a location of the axis and expresses information corresponding to the region of interest, wherein the object is a consolidation of multiple objects of a same function as the object, as each of the multiple objects would have represented a different detected region of interest.

14. A non-transitory, tangible computer-readable recording medium on which a program for causing, when read by a computer, the computer to perform the image processing method according to claim 13 is recorded.

* * * * *